(12) United States Patent
Basu

(10) Patent No.: US 10,362,953 B2
(45) Date of Patent: Jul. 30, 2019

(54) ELECTRODE ARRAY CATHETER WITH INTERCONNECTED FRAMEWORK

(71) Applicant: Biosense Webster (Israel) Ltd., Yokneam (IL)

(72) Inventor: Shubhayu Basu, Anaheim, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 316 days.

(21) Appl. No.: 14/966,220

(22) Filed: Dec. 11, 2015

(65) Prior Publication Data

US 2017/0164858 A1 Jun. 15, 2017

(51) Int. Cl.

| | | |
|---|---|---|
| *A61B 5/042* | (2006.01) |
| *A61B 18/14* | (2006.01) |
| *A61B 5/00* | (2006.01) |
| A61B 18/00 | (2006.01) |
| A61B 34/20 | (2016.01) |

(52) U.S. Cl.
CPC .......... *A61B 5/0422* (2013.01); *A61B 5/6858* (2013.01); *A61B 5/6859* (2013.01); *A61B 18/14* (2013.01); *A61B 18/1492* (2013.01); *A61B 2018/0016* (2013.01); *A61B 2018/00267* (2013.01); *A61B 2018/00351* (2013.01); *A61B 2018/00577* (2013.01); *A61B 2018/00839* (2013.01); *A61B 2034/2051* (2016.02); *A61B 2505/05* (2013.01)

(58) Field of Classification Search
CPC ... A61B 5/0422; A61B 5/6858; A61B 5/6859; A61B 18/1492
See application file for complete search history.

(56) References Cited

U.S. PATENT DOCUMENTS

| | | | |
|---|---|---|---|
| 4,890,623 A | | 1/1990 | Cook et al. |
| 5,345,936 A | * | 9/1994 | Pomeranz ............ A61B 5/0422 600/374 |
| 5,391,199 A | | 2/1995 | Ben-Haim |
| 5,702,438 A | * | 12/1997 | Avitall ............... A61B 18/1492 600/374 |
| 5,772,590 A | | 6/1998 | Webster |
| 6,064,905 A | | 5/2000 | Webster et al. |
| 6,239,724 B1 | | 5/2001 | Dron et al. |
| 6,332,089 B1 | | 12/2001 | Acker et al. |
| 6,484,118 B1 | | 11/2002 | Govari |

(Continued)

FOREIGN PATENT DOCUMENTS

| | | |
|---|---|---|
| EP | 2641556 A1 | 9/2013 |
| WO | 94/06349 A1 | 3/1994 |

(Continued)

OTHER PUBLICATIONS

European Search Report from corresponding European Patent Application 16203110.8, dated Apr. 19, 2017, pp. 1-8.

*Primary Examiner* — Lee S Cohen

(74) *Attorney, Agent, or Firm* — Dergosits & Noah LLP; Todd A. Noah

(57) ABSTRACT

This disclosure includes a catheter with an electrode array formed by an interconnected framework. The framework may have a plurality of elements interconnected by a plurality of junctions at locations intermediate the proximal and distal ends of the electrode array assembly. The electrodes may be printed on a polymeric layer of the interconnected framework.

16 Claims, 7 Drawing Sheets

(56) References Cited

U.S. PATENT DOCUMENTS

| | | |
|---|---|---|
| 6,618,612 B1 | 9/2003 | Acker et al. |
| 6,669,693 B2 * | 12/2003 | Friedman ............ A61B 18/1492 606/41 |
| 6,690,963 B2 | 2/2004 | Ben-Haim et al. |
| 6,748,255 B2 | 6/2004 | Fuimaono et al. |
| 6,961,602 B2 | 11/2005 | Fuimaono et al. |
| 6,973,340 B2 | 12/2005 | Fuimaono et al. |
| 7,393,352 B2 | 7/2008 | Berube |
| 7,615,049 B2 * | 11/2009 | West ................. A61B 18/1492 606/41 |
| 8,147,486 B2 | 4/2012 | Honour et al. |
| 8,412,307 B2 | 4/2013 | Willis et al. |
| 8,447,377 B2 * | 5/2013 | Harlev ................. A61B 5/0422 29/825 |
| 8,755,861 B2 | 6/2014 | Harlev et al. |
| 9,480,790 B2 * | 11/2016 | Machado ............ A61N 1/36114 |
| 2002/0065455 A1 | 5/2002 | Ben-Haim et al. |
| 2003/0018330 A1 * | 1/2003 | Swanson ............ A61B 18/1492 606/41 |
| 2003/0120150 A1 | 6/2003 | Govari |
| 2004/0068178 A1 | 4/2004 | Govari |
| 2006/0106298 A1 * | 5/2006 | Ahmed ................ A61B 5/0422 600/381 |
| 2011/0172658 A1 | 7/2011 | Gelbart et al. |
| 2013/0190587 A1 | 7/2013 | Lopes et al. |
| 2014/0194716 A1 * | 7/2014 | Diep .................... A61B 5/6859 600/374 |
| 2015/0208937 A1 * | 7/2015 | Bullinga ............. A61B 5/0408 600/424 |
| 2015/0265334 A1 | 9/2015 | Franke et al. |
| 2017/0035496 A1 * | 2/2017 | Nagale ............... A61B 18/1485 |
| 2017/0035497 A1 * | 2/2017 | Nagale ............... A61B 18/1492 |

FOREIGN PATENT DOCUMENTS

| | | |
|---|---|---|
| WO | 96/05768 | 2/1996 |
| WO | 2004/078066 A2 | 9/2004 |
| WO | 2008141150 A2 | 11/2008 |
| WO | 2014118733 A2 | 8/2014 |
| WO | 2015-187430 A2 | 12/2015 |

* cited by examiner

ELECTRODE ARRAY CATHETER WITH INTERCONNECTED FRAMEWORK

FIELD OF THE PRESENT DISCLOSURE

This invention relates to electrophysiologic (EP) catheters, in particular, EP catheters for mapping electrical signals and/or ablating tissue in the heart.

BACKGROUND

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector. Mapping the activation front and conduction fields aids the physician in identifying and diagnosing abnormalities, such as ventricular and atrial tachycardia and ventricular and atrial fibrillation, which may result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated so as to restore the normal function of the heart insofar as is possible. As an illustration, cardiac arrhythmias including atrial fibrillation, may occur when regions of cardiac tissue abnormally conduct electric signals to adjacent tissue, thereby disrupting the normal cardiac cycle and causing asynchronous rhythm. Procedures for treating arrhythmia include disrupting the origin of the signals causing the arrhythmia, as well as disrupting the conducting pathway for such signals, such as by forming lesions to isolate the aberrant portion. Thus, by selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

A number of advantages may be obtained by providing a catheter having multiple electrodes to allow for mapping larger regions and/or for creating a plurality of lesions either simultaneously or without the need to reposition the catheter. One suitable configuration described in commonly assigned U.S. Pat. No. 6,961,602, which is herein incorporated by reference, employs a catheter having a multiray electrode assembly formed by a plurality of spines each carrying one or more diagnostic or ablation electrodes. The assembly has two or more spines, each having a proximal end attached at the distal end of the catheter body and a free distal end. Another configuration that has been employed is known as a basket-shaped electrode assembly. Examples are described in commonly assigned U.S. Pat. Nos. 5,772,590, 6,748,255 and 6,973,340, the entire disclosures of each of which are incorporated herein by reference. Basket catheters also employ a plurality of spines, which are connected at their distal end as well as the proximal end. In either configuration, the spines may be arranged in an expanded arrangement wherein at least a portion of each spine extends radially outwardly from the catheter body or in a collapsed arrangement wherein each spine is disposed generally along the longitudinal axis of the catheter body. The collapsed arrangement facilitates advancing the electrode assembly to the desired location in the patient's body, such as through the vasculature in a percutaneous approach. When the electrode assembly assumes the expanded arrangement, one or more of the electrodes on the spines are brought into contact with tissue to allow for measurement of electrical signals and/or ablation of tissue.

By employing multiple spines, these electrode assemblies are adapted to provide an array of electrodes to occupy a three dimensional space defined by the anatomy of the patient, such as a chamber of the heart or an ostium vessel for example. Generally, it would be desirable to deploy the spines, and correspondingly the electrodes, in a defined configuration to obtain any number of benefits, such as to provide coverage of the deployed area with certain density of electrodes, to provide concentrated coverage in a specific region, to help determine the location of the electrodes with respect to each other, to more closely conform to the volume in which it is deployed, or any others. However, conventional multiple spine electrode assemblies may not deploy with the spines in the intended configuration, creating a suboptimal array of electrodes. For example, in a multiray electrode assembly, the spines are secured in relation to each other only at the proximal end, while in a basket-shaped electrode assembly, they are secured only at their proximal and distal ends. As such, the spines may not assume their intended radial distribution, particularly at locations that are farther away from the secured ends. Notably, the spines may bunch together more closely or may splay apart to a greater degree than desired. The tendency of the multiple spine electrode assemblies to assume such unintended distributions may be exacerbated by irregularities in a patient's anatomy.

Accordingly, there is a need for an electrode array assembly that has improved stability. For example, it would be desirable to provide an electrode array assembly in which the electrodes have a greater tendency to remain in defined relationships with each other. The techniques of this disclosure as described in the following materials satisfy these and other needs.

SUMMARY

The present disclosure includes a catheter with an elongated catheter body having a proximal end, a distal end and an electrode array assembly having a proximal end and a distal end mounted at the distal end of the catheter body. The electrode array assembly may be formed by an interconnected framework having a plurality of elements interconnected by a plurality of junctions at locations intermediate the proximal and distal ends of the electrode array assembly, wherein the interconnected framework has a collapsed configuration in which the elements are arranged generally along a longitudinal axis of the catheter body and an expanded configuration in which the elements are positioned radially outwards from the longitudinal axis to deploy an array of electrodes mounted on the interconnected framework.

In one aspect, each element of the interconnected framework has a reduced free length between junctions. The reduced free length may be less than half of a length of a shortest contour line extending from a proximal end to a distal end of the electrode array assembly. Further, the reduced free length may be less than a third of a length of a shortest contour line extending from a proximal end to a distal end of the electrode array assembly.

In one aspect, the interconnected framework may include a polymeric layer and a plurality of printed electrodes. The interconnected framework may also have a substrate upon which the polymeric layer is applied. The substrate may be monolithic. For example, the substrate may be a cut tube. Further, the substrate may be formed from a shape memory material. Accordingly, the interconnected framework may be a flexible circuit.

In one aspect, the interconnected framework may have at least one junction between interconnected elements at a distal end of electrode array assembly to define a closed shape. The junctions between interconnected elements may be concentrated at a polar region or may be distributed substantially evenly across the interconnected framework.

In one aspect, the interconnected framework may include a plurality of free distally projecting rays.

This disclosure also includes a method for treatment that may involve providing a catheter with an elongated catheter body having a proximal end, a distal end and an electrode array assembly mounted at the distal end of the catheter body with an interconnected framework having a plurality of elements interconnected by a plurality of junctions at locations intermediate the proximal and distal ends of the electrode array assembly, advancing the distal end of the catheter with the electrode array assembly to a desired region within a patient with the interconnected framework in a collapsed configuration in which elements of the interconnected framework are arranged generally along a longitudinal axis of the catheter body and causing the electrode array assembly to assume an expanded configuration in which the elements are positioned radially outwards from the longitudinal axis of the catheter body to deploy an array of electrodes mounted on the interconnected framework so that at least one electrode is in contact with tissue.

In one aspect, electrical signals may be received from the at least one electrode in contact with tissue.

In one aspect, radio frequency energy may be delivered to the at least one electrode in contact with tissue to form a lesion.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
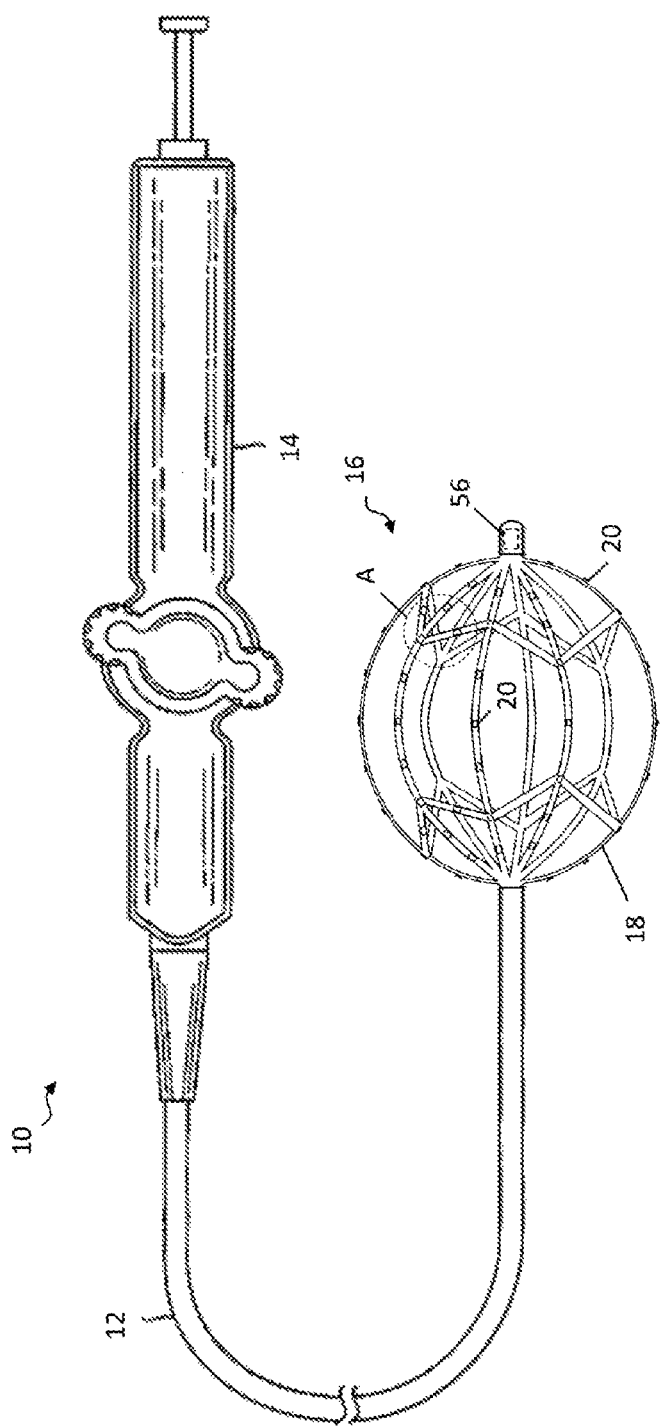
FIG. 1 is a top plan view of a catheter with an electrode array assembly, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

As noted above, certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket-shaped electrode assembly having a high electrode density may be used to accurately map this electrical activity. Further, RF energy may be delivered to selected treatment areas for ablation based therapies, including for example, isolation of a source of irregular electrical signals by blocking electrical conduction. Focal ablations using unipolar devices benefit from targeted delivery of RF energy along with localized feedback of catheter placement, both spatially and with respect to tissue engagement. However, focal ablation procedures typically involve relative long procedure times as a result of the physician needing to stitch a series of "quantized" RF ablation to form a lesion having the desired characteristics, such as the creation of a continuous circumferential block which surrounds the ostium of the targeted vein. Additionally, the use of a focal unipolar electrode requires substantial physician skill levels augmented with peripheral navigation systems in order to accurately and reliably position the electrodes. Correspondingly, a multielectrode device may present the opportunity to simultaneously record electrical signals and/or deliver ablation energy at a plurality of locations. As will be described herein, this disclosure is directed to a catheter having an electrode array assembly having an interconnected framework to help stabilize the electrodes when deployed. In particular, the interconnected framework employs a plurality of elements, each of which may have a reduced free length between interconnections to help stabilize the framework.

To help illustrate aspects of this disclosure, an exemplary embodiment of an electrophysiologic catheter with an electrode array assembly is shown schematically in FIG. 1. Catheter 10 comprises an elongated catheter body 12 having proximal and distal ends, a control handle 14 at the proximal end of the catheter body 12, and an electrode array assembly 16 comprising an interconnected framework 18 mounted at the distal end of the catheter body 12. Mounted on interconnected framework 18 are a plurality of electrodes 20, forming an electrode array.

Figure 2:
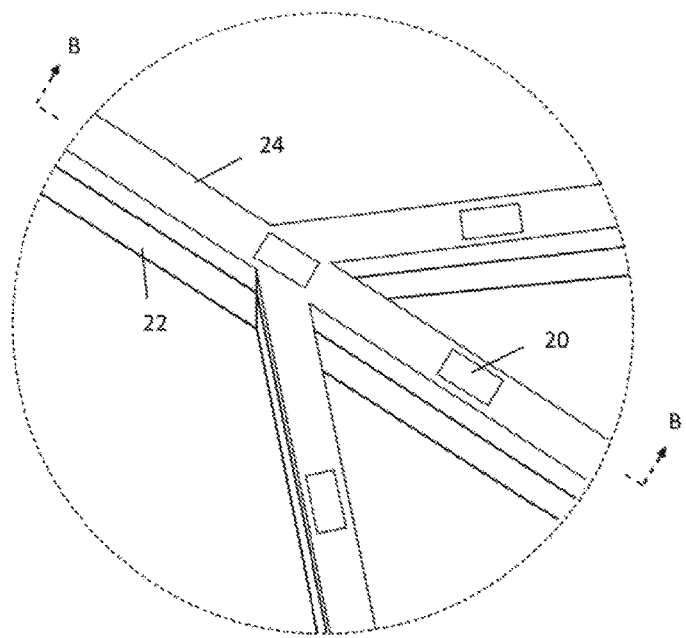
FIG. 2 is a detail view of a junction between interconnecting elements of the electrode array assembly, according to one embodiment.
Figure 3:
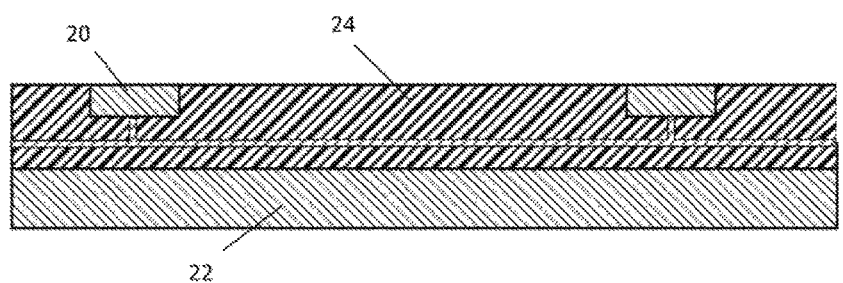
FIG. 3 is a cross section of the junction of FIG. 2.

Details of electrodes 20 and interconnected framework 18 are shown in FIGS. 2 and 3. A detail of region A of FIG. 1 is illustrated in FIG. 2. Interconnected framework 18 may be formed from a structural substrate 22 with a polymeric layer 24 constructed using techniques to create flexible circuits, or "flex circuits," known in the art. Polymeric layer 24 may be any suitable flexible polymer, such as polyester, polyimide, polyethylene napthalate (PEN), polyetherimide (PEI), fluoropolymers (FEP), PEEK or the like, including copolymers. Generally, polymeric layer 24 may be provided with conductive elements, such as electrodes 20, as well as leads, traces and the like, as desired using metallic foil and photolithography or equivalent techniques, although suitable patterns of conductive tape may be laminated between layers of polymer or electro-deposition methods may also be used. A cross section taken along line B-B is depicted in FIG. 3. As may be seen, polymeric layer 24 is applied over substrate 22 and electrodes 20 are printed on top. Depending on the embodiment, electrodes 20 may be relatively flush with the surface of polymeric layer 24 or may protrude to facilitate tissue engagement. Electrodes 20 may be configured as unipolar, bipolar or both and may be diagnostic electrodes, ablation electrodes, reference electrodes or others, or may be multifunctional. If different electrode configurations are employed, any combination and number of different configurations may be provided as warranted by the intended application. By employing the flex circuit techniques, any number of electrodes 20 may be readily positioned at any location on interconnected framework 18. For example, electrodes 20 may be positioned on the interconnected framework and spaced equally from each other at a distance of approximately 4 mm to allow for mapping of an area in which catheter is deployed.

In the embodiment shown in FIG. 1, electrode array assembly 18 may have a configuration similar to conventional basket-shaped electrode assemblies, so that interconnected framework 18 may have a collapsed configuration in which the elements forming interconnected framework 18 are disposed generally along a longitudinal axis of the catheter body 12 so that the spines are capable of fitting within a lumen of a guiding sheath, as discussed further below. Further, interconnected framework 18 may have an expanded configuration when deployed to present the array of electrodes 20. Interconnected framework 18 may have a generally spherical, ovoid, ellipsoidal or other closed shape, but may also be designed to take on other shapes which may be regular or irregular as well as being open or closed. For example, as described below, an interconnected framework embodying aspects of this disclosure may be configured to have an open distal end with multiple rays. Interconnected framework 18 may also have different sizes when expanded for deployment depending on the patient's anatomy to provide a close fit to the area of the patient being investigated, such as the right or left atria.

Depending on the embodiment, the transition between the collapsed configuration and the expanded configuration may be caused by the characteristics of interconnected framework 18, by mechanistic actuation or by a combination. For example, interconnected framework 18 may have a pre-shaped configuration when not restrained by a guiding sheath, causing it to expand radially outwards to assume the expanded configuration. Alternatively, a mechanism, such as a puller wire, may be used to adjust the relative distance between the distal and proximal ends of interconnected framework 18, causing it to bow outwards into the expanded arrangement.

Accordingly, substrate 22 may be formed form a shape memory material to help interconnected framework 18 assume the expanded and collapsed configurations. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature.

Accordingly, electrode array assembly 16 may have a three dimensional shape that can be easily collapsed to be fed into a guiding sheath and then readily returned to its expanded shape memory configuration upon delivery to the desired region of the patient upon removal of the guiding sheath. In some embodiments, interconnected framework 18 may be formed from a nitinol hypotube by laser cutting or other similar techniques, to provide a monolithic framework. For example, depending on the embodiment, a 3 mm tube having a wall thickness of approximately 8 to 9 mil may be used to form interconnected substrate 22. One of skill in the art will understand that tubes with other diameters and wall thicknesses may be used to form interconnected substrate 22. As an example of an alternative construction, polymeric layer 24 may have sufficient resilient characteristics to permit substrate 22 to be omitted. One exemplary material for such embodiments may be PEEK, such that interconnected framework 18 may be cut from a tube of PEEK or by using any other suitable technique.

Figure 4:
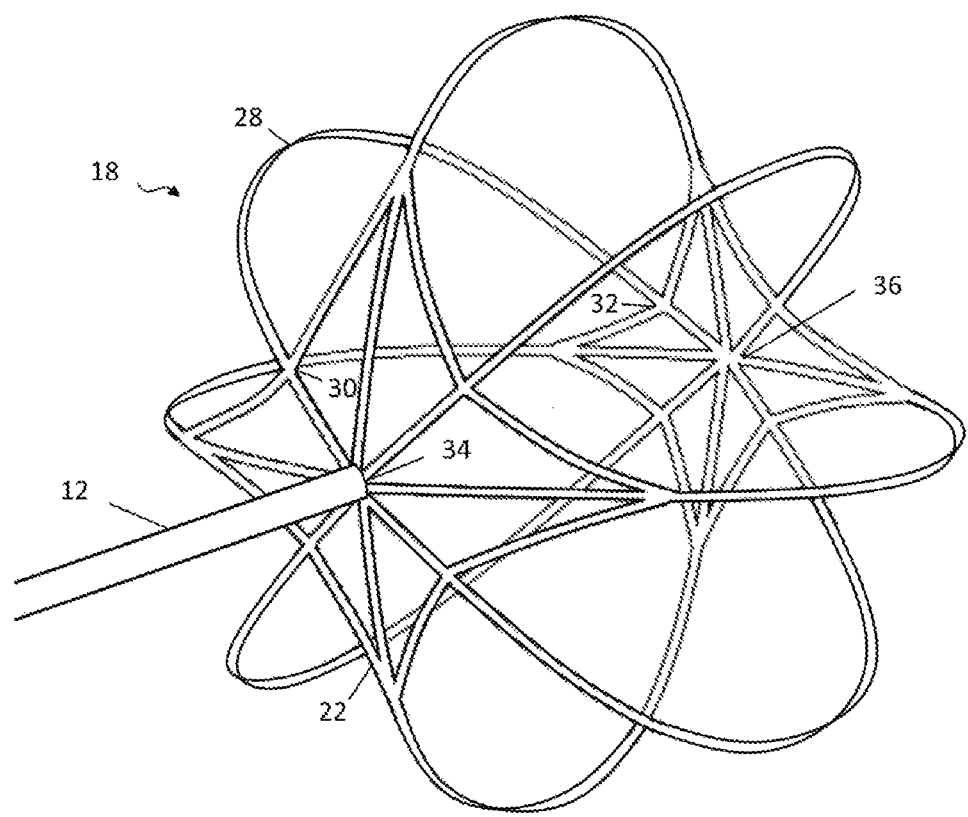
FIG. 4 is a perspective view of the substrate of an electrode array assembly, according to one embodiment.

A perspective view of substrate 22 of interconnected framework 18 is shown FIG. 4 in its expanded, deployed configuration. As will be appreciated, the interconnections between elements of the framework help stabilize the deployed configuration and accordingly, electrode array assembly 16. Any number of different interconnection designs to form a network of structural elements may be employed with the techniques of this disclosure. To form interconnected framework 18, junctions between interconnecting elements are located at locations intermediate between the proximal and distal ends of electrode array assembly 16. One characteristic of interconnected framework 18 is that the free length of any element is shorter than the shortest contour line over a surface defined by interconnected framework 18. In the context of FIG. 4, for example, element 28 that extends between interconnection junction 30 and interconnection junction 32. Interconnected framework 18 defines a generally spherical surface, although interconnected framework 18 may be configured to assume other deployed shapes as noted above. Accordingly, the spherical surface may be seen to have a proximal pole 34 where electrode array assembly is joined to catheter body 12 and an opposing distal pole 36. In a conventional basket-shaped electrode assembly, a deflected spine would lie on a surface of the sphere, corresponding to the shortest contour line between the poles, extending from proximal pole 34 at its proximal end to distal pole 36 at its distal end. Alternatively, this distance may be appreciated to be the meridian distance or a suitable equivalent with regard to other deployed shapes. As such, essentially the entire length of the spine would be free. In contrast, element 28, even though it may have the longest free length or it may equal the longest free length within interconnected framework 18, has a reduced free length in comparison. As an example, in some embodiments the reduced free length may be one half or less the corresponding length of the shortest contour line and in other embodiments may be one third or less. Given that each element of interconnected framework 18 is has at most this reduced free length, it will be appreciated that the elements will experience less tendency to deflect from the intended deployed shape, resulting in a more stable electrode array assembly 16.

In light of the above discussion, it may be seen that each element has at least one interconnection with other elements in order to form the network of interconnected framework 18. Any desired pattern of interconnecting elements may be employed. In one aspect, the elements may be formed by laser cutting a tube as noted above. By increasing the number of interconnecting elements, interconnected framework 18 may occupy more of the surface defined by the deployed shape, which in turn presents more flexibility in placement of electrodes 20 and may allow for an increased density of electrodes in the array. Conversely, decreasing the number of interconnecting elements may increase the overall conformability of electrode array assembly 16 to adjust to the space in which it deployed, while still increasing the stability of the array as compared to conventional designs. A suitable balance between these design constraints may be employed as warranted by the intended application.

Figure 5:
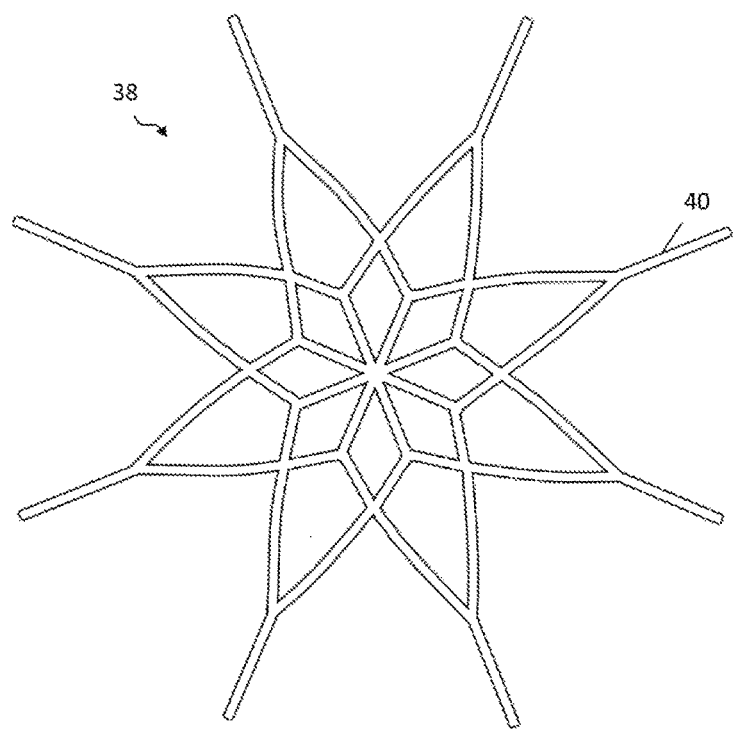
FIG. 5 is a schematic view of a first pattern of interconnections of an electrode array assembly, according to one embodiment.
Figure 6:
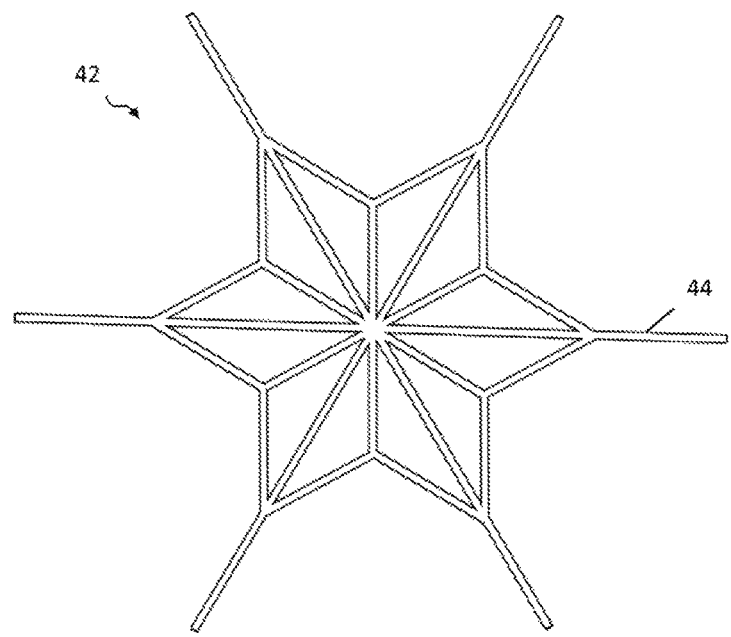
FIG. 6 is a schematic view of a second pattern of interconnections of an electrode array assembly, according to one embodiment.
Figure 7:
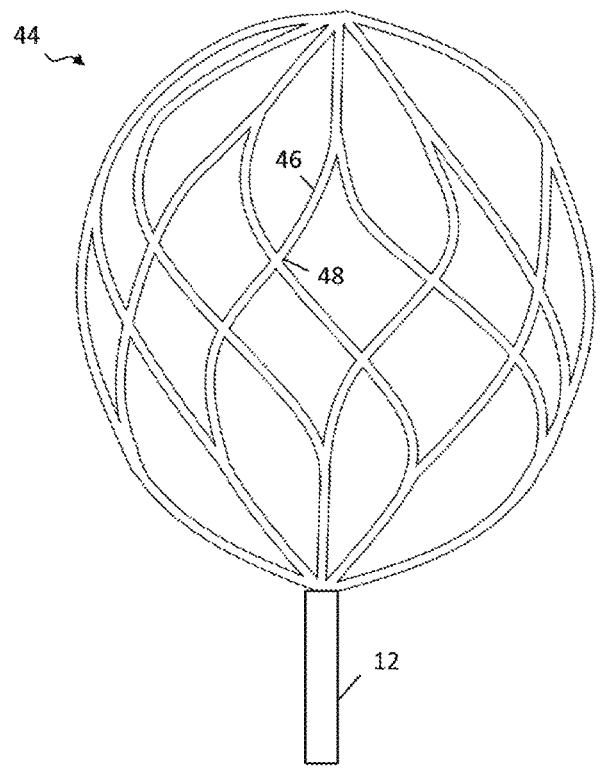
FIG. 7 is a schematic view of evenly distributed junctions in an electrode array assembly, according to one embodiment.

As shown in FIG. 4, a greater number of interconnections may be provided adjacent the poles (or equivalent structures associated with other shapes that may be employed) or may be more evenly distributed. As illustration only and without limitation, another suitable pattern of interconnecting elements and junctions formed by substrate 38 is shown in the polar view of FIG. 5, in which one hemisphere has been flattened and in which the interconnections are concentrated in the polar region. As may be seen, substrate 38 has eight radiating elements 40 that extend towards the opposite pole, where the interconnection pattern may be repeated or a different pattern may be employed. Yet another exemplary pattern is depicted in the polar view of FIG. 6, showing substrate 42. Although similar, this configuration results in six radiating elements 42. As a contrasting example, FIG. 7 shows one half of substrate 44 in its deployed and expanded configuration. Although this configuration also assumes a shape similar to that of a conventional basket-shaped electrode assembly, the pattern of interconnecting elements 46 in this embodiment exhibits a more even distribution of junctions 48 across the surface.

Figure 8:
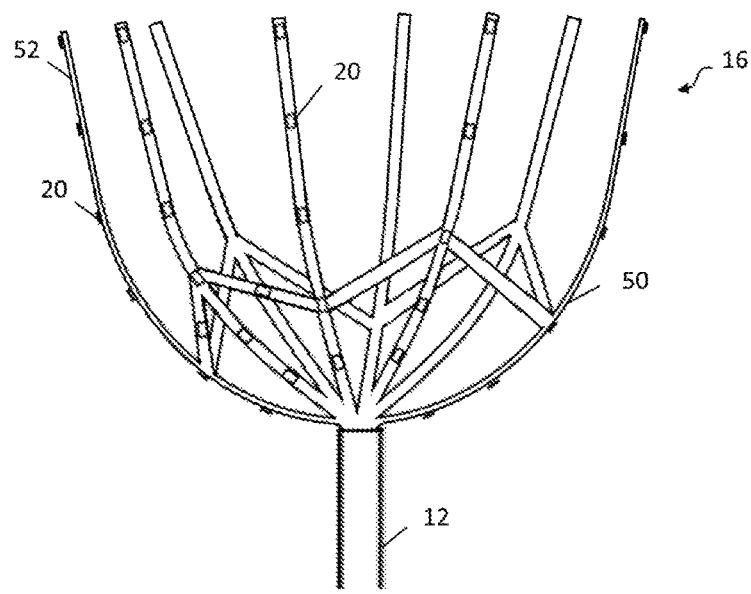
FIG. 8 is a schematic view of an electrode array assembly having a plurality of distally projecting rays, according to one embodiment.

Although the above embodiments have been described in comparison to conventional basket-shaped electrode assemblies, one of skill in the art will recognize that an interconnected framework embodying the techniques of this disclosure may be used to create other electrode assembly configurations. As noted above, conventional multiray electrode assemblies may involve a plurality of spines that radiate from a proximal connection point with free distal ends. A similar configuration may be achieved as shown in FIG. 8, with an electrode array assembly 16 formed by interconnected framework 50. Interconnections adjacent the connection to catheter body 12 help stabilize interconnected framework 50, while presenting distally projecting rays 52 that may more easily conform to tissue defining the space in which electrode array assembly 16 is deployed to engage electrodes 20 with tissue. Rays 52 have free ends and may be configured to radiate outwards from the longitudinal axis of catheter body 20 to any desired degree. In this context, the distal end of interconnected framework 50 is defined by the distal ends of rays 52, such that the shortest contour line across the surface of electrode array assembly 16 would originate at the proximal connection to catheter body 12 and extend to the distal end of interconnected framework 50. Correspondingly, the elements of interconnected framework 50 having the longest free length may be rays 52, which exhibit a reduced free length as compared to the shortest contour line. As with the other embodiments described above, interconnected framework 50 may be formed by cutting a tube of material, such as a nitinol hypotube.

Catheter body 12 comprises an elongated tubular construction having a single, axial or central lumen but can optionally have multiple lumens along all or part of its length if desired. Catheter body 12 is flexible, i.e., bendable, but substantially non-compressible along its length. Catheter body 12 can be of any suitable construction and made of any suitable material, such as by using an outer wall of polyurethane or PEBAX® (polyether block amide). The wall may have an imbedded braided mesh of stainless steel or the like, as is generally known in the art, to increase torsional stiffness of the catheter body 12 so that, when the control handle 14 is rotated, the distal end of the catheter body 12 will rotate in a corresponding manner.

The length of the catheter body 12 is not critical, but may range from about 90 cm to about 120 cm, such as about 110 cm. The outer diameter of the catheter body 12 is also not critical, but generally be adapted to present an outer diameter sufficient to accommodate the construction of electrode array assembly 16 and any associated leads, irrigation lumens, puller wires, position or other sensors and the like while retaining an insertion profile that allows advancement through the patient's vasculature. In some embodiments, catheter body 12 may be about 10 french or less, such as 8 french or 7 french. Likewise, the thickness of the outer wall of catheter body 12 is not critical but may be thin enough provide a lumen or lumens of sufficient size. An example of a catheter body construction suitable for use in connection with the present invention is described and depicted in U.S. Pat. No. 6,064,905, the entire disclosure of which is incorporated herein by reference.

Figure 9:
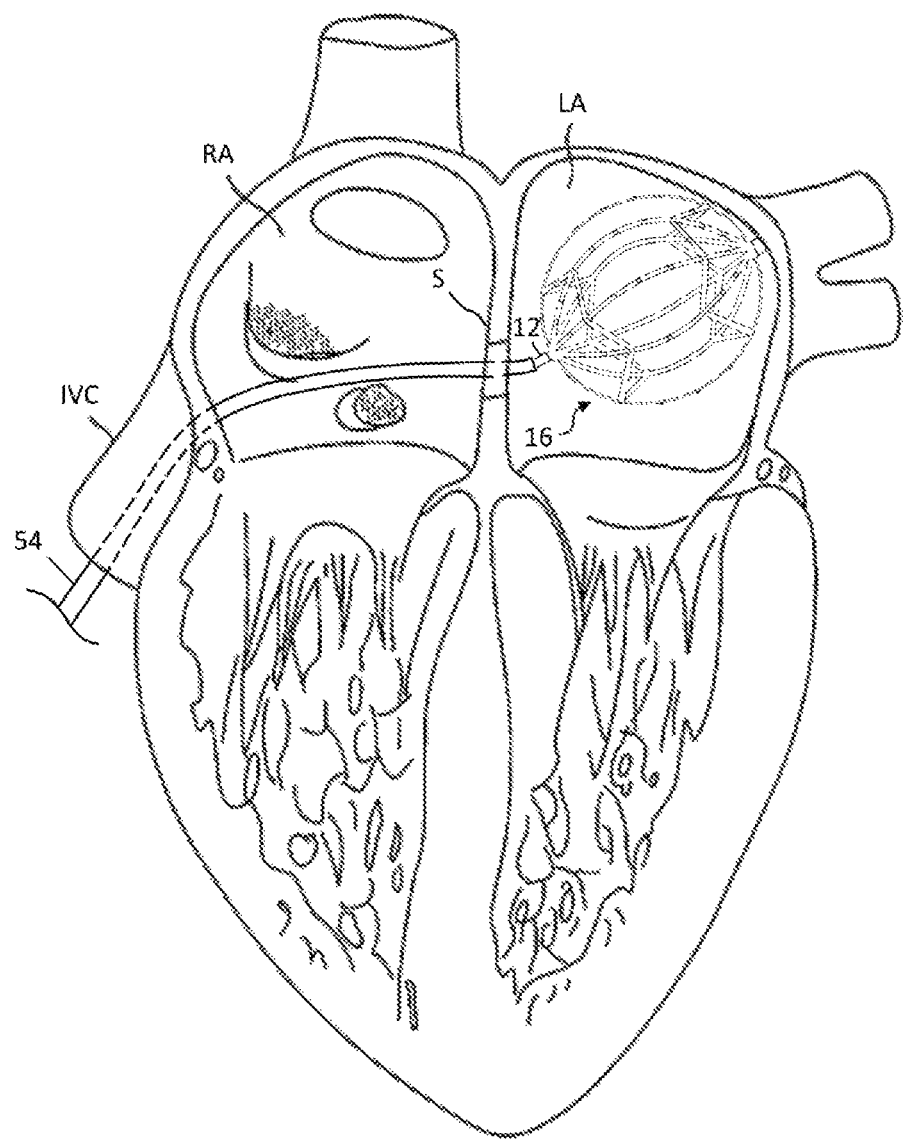
FIG. 9 is a schematic view of an electrode array assembly positioned within the left atrium, according to one embodiment.

In one aspect, an electrophysiologist may introduce a guiding sheath, guidewire and dilator into the patient, as is generally known in the art. As an example, a guiding sheath for use in connection with the inventive catheter is an appropriately-sized PREFACE™ Braided Guiding Sheath (commercially available from Biosense Webster, Inc., Diamond Bar, Calif.). The guidewire is inserted, the dilator is removed, and the catheter is introduced through the guiding sheath whereby the guidewire lumen in the expander permits the catheter to pass over the guidewire. In one exemplary procedure as depicted in FIG. 9, the catheter is first introduced to the patient's heart (H) through the right atrium (RA) via the inferior vena cava (IVC), where it passes through the septum (S) in order to reach the left atrium (LA). As will be appreciated, electrode array assembly 16 may be deflected into a straightened configuration and constrained within guiding sheath 54 to allow catheter 10 to be passed through the patient's vasculature to the desired location. Once the distal end of the catheter reaches the desired location, e.g., the left atrium, guiding sheath 54 is withdrawn to expose the electrode array assembly 16, allowing it to be deployed, assuming the expanded configuration. As will be appreciated, a procedure employing an electrode array assembly with the techniques of this disclosure may be performed, and may include any desired operation involving measuring electrical signals and/or ablating tissue within a patient. For example, by using the electrode array assembly with interconnected framework, the electrophysiologist can obtain a true anatomy of a cavernous region of the heart, including an atrium, from the electrodes allowing a more rapid mapping of the region.

Figure 10:
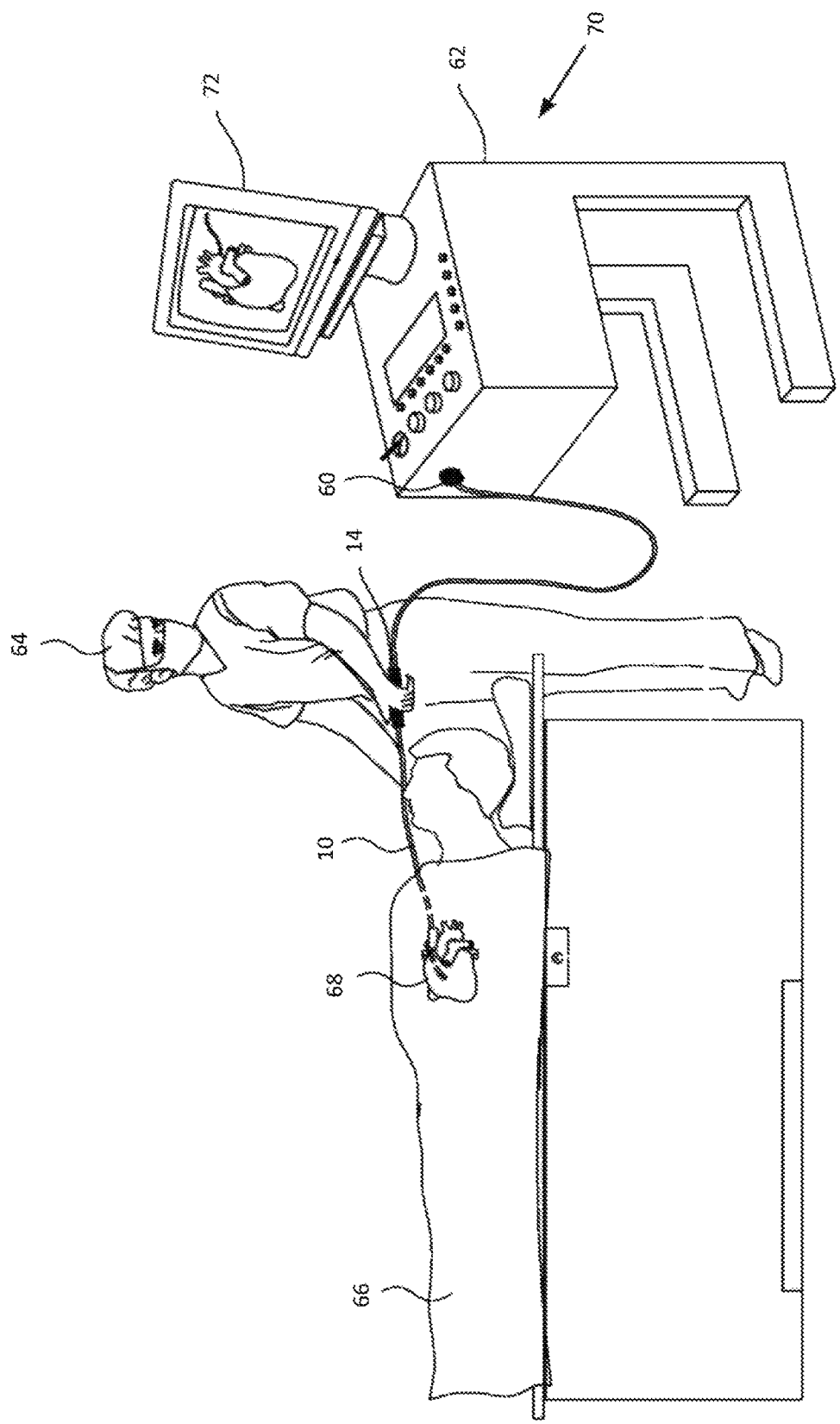
FIG. 10 is a schematic illustration of an invasive medical procedure using an electrode array assembly, according to one embodiment.

To help illustrate use of the electrode array assembly 16, FIG. 10 is a schematic depiction of an invasive medical procedure, according to an embodiment of the present invention. Catheter 10, with the electrode array assembly 16 (not shown in this view) at the distal end may have a connector 60 at the proximal end for coupling the leads of the electrodes and sensors (not shown in this view) to a console 62 for recording and analyzing the signals they detect as well as for supplying ablating energy. An electrophysiologist 64 may insert the catheter 10 into a patient 66 in order to acquire electropotential signals from the heart 68 of the patient. The electrophysiologist 64 uses the control handle 14 attached to the catheter in order to perform the insertion. Console 62 may include a processing unit 70 which analyzes the received signals, and which may present results of the analysis on a display 72 attached to the console. The results are typically in the form of a map, numerical displays, and/or graphs derived from the signals. Processing unit 70 may also control the delivery of energy to electrode(s) 20 for creating one or more lesions, such as at locations associated with abnormal electrical activity identified by analyzing received signals.

Further, the processing unit 70 may also receive signals from one or more position sensors, such as sensor 56 (as shown in FIG. 1). The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 70 to determine the position, (e.g., the location and orientation) of the distal end of catheter 10 within the heart cavity. The electrophysiologist may then view the position of the electrode array assembly 16 on an image the patient's heart on the display 72. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with respect to electrode array assembly 16. The coordinates of the distal sensor relative to the proximal sensor may be determined and, with other known information pertaining to the configuration of electrode array assembly 16, used to find the positions of each of the electrodes 20.

The preceding description has been presented with reference to presently disclosed embodiments of the invention. Those skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
  an elongated catheter body having a proximal end, a distal end; and
  an electrode array assembly having a plurality of electrodes, a proximal end and a distal end mounted at the distal end of the catheter body and comprising an interconnected framework having a plurality of elements interconnected by a plurality of junctions at locations intermediate the proximal and distal ends of the electrode array assembly, the interconnected framework comprising a polymeric layer and a plurality of printed electrodes positioned on all connected elements of at least some of the junctions, wherein the interconnected framework has a collapsed configuration in which the elements are arranged generally along a longitudinal axis of the catheter body and an expanded configuration in which the elements are positioned radially outwards from the longitudinal axis to deploy the array of electrodes mounted on the interconnected framework.

2. The catheter of claim 1, wherein each element of the interconnected framework has a reduced free length between junctions.

3. The catheter of claim 2, wherein the reduced free length is less than half of a length of a shortest contour line extending from a proximal end to a distal end of the electrode array assembly.

4. The catheter of claim 3, wherein the reduced free length is less than a third of a length of a shortest contour line extending from a proximal end to a distal end of the electrode array assembly.

5. The catheter of claim 1, wherein the interconnected framework further comprises a substrate upon which the polymeric layer is applied.

6. The catheter of claim 5, wherein the substrate is monolithic.

7. The catheter of claim 5, wherein the substrate comprises a cut tube.

8. The catheter of claim 5, wherein the substrate comprises a shape memory material.

9. The catheter of claim 1, wherein the interconnected framework comprises a flexible circuit.

10. The catheter of claim 1, wherein the interconnected framework comprises at least one junction between interconnected elements at a distal end of electrode array assembly to define a closed shape.

11. The catheter of claim 10, wherein the junctions between interconnected elements are concentrated at a polar region.

12. The catheter of claim 10, wherein the junctions between interconnected elements are distributed substantially evenly across the interconnected framework.

13. The catheter of claim 1, wherein the interconnected framework comprises a plurality of free distally projecting rays.

14. A method for treatment comprising:
providing a catheter with an elongated catheter body having a proximal end, a distal end and an electrode array assembly mounted at the distal end of the catheter body with an interconnected framework having a plurality of elements interconnected by a plurality of junctions at locations intermediate the proximal and distal ends of the electrode array assembly, the interconnected framework comprises a polymeric layer and a plurality of printed electrodes positioned on all connected elements of at least some of the junctions,
advancing the distal end of the catheter with the electrode array assembly to a desired region within a patient with the interconnected framework in a collapsed configuration in which elements of the interconnected framework are arranged generally along a longitudinal axis of the catheter body; and
causing the electrode array assembly to assume an expanded configuration in which the elements are positioned radially outwards from the longitudinal axis of the catheter body to deploy an array of electrodes mounted on the interconnected framework so that at least one electrode is in contact with tissue.

15. The method of claim 14, further comprising receiving electrical signals from the at least one electrode in contact with tissue.

16. The method of claim 14, further comprising delivering radio frequency energy to the at least one electrode in contact with tissue to form a lesion.

* * * * *